United States Patent [19]
Andrus et al.

[11] Patent Number: 5,895,356
[45] Date of Patent: Apr. 20, 1999

[54] APPARATUS AND METHOD FOR TRANSURETHRAL FOCUSSED ULTRASOUND THERAPY

[75] Inventors: W. Scott Andrus; Claude Tihon, both of Eden Prairie; Claire T. Hovland, Minnetonka, all of Minn.; Charles S. Desilets, Edmonds, Wash.

[73] Assignee: American Medical Systems, Inc., Minnetonka, Minn.

[21] Appl. No.: 08/559,749

[22] Filed: Nov. 15, 1995

[51] Int. Cl.⁶ .............................. A61B 8/02; A61N 7/00
[52] U.S. Cl. .............................. 600/439; 601/3
[58] Field of Search .................. 128/660.03, 662.03, 128/662.06; 601/3; 607/96–97, 101; 604/22; 600/439, 459, 462–3, 471, 105, 135

[56] References Cited

U.S. PATENT DOCUMENTS

| | | | |
|---|---|---|---|
| 4,858,613 | 8/1989 | Fry et al. | 128/660.03 |
| 5,036,855 | 8/1991 | Fry et al. | 128/660.03 |
| 5,316,000 | 5/1994 | Chapelon et al. | 600/439 |
| 5,344,435 | 9/1994 | Turner et al. | 607/101 |
| 5,370,675 | 12/1994 | Edwards et al. | 607/101 |
| 5,385,544 | 1/1995 | Edwards et al. | 607/101 X |
| 5,391,196 | 2/1995 | Devonec | 607/101 X |
| 5,391,197 | 2/1995 | Burdette et al. | 601/3 |
| 5,470,350 | 11/1995 | Buchholz et al. | 128/660.03 X |
| 5,471,988 | 12/1995 | Fujio et al. | 128/660.03 |
| 5,474,071 | 12/1995 | Chapelon et al. | 128/660.03 |
| 5,492,126 | 2/1996 | Hennige et al. | 128/662.06 |
| 5,542,916 | 8/1996 | Hirsch et al. | 607/101 X |
| 5,573,497 | 11/1996 | Chapelon | 607/97 X |
| 5,601,526 | 2/1997 | Chapelon et al. | 601/2 X |
| 5,643,179 | 7/1997 | Fujimoto | 601/2 |

Primary Examiner—Francis J. Jaworski
Attorney, Agent, or Firm—Oppenheimer Wolff & Donnelly

[57] ABSTRACT

An apparatus and method for the treatment of diseases of the prostate, including BPH and prostate cancer, utilizing transurethrally applied focussed ultrasound energy to produce hyperthermal and thermotherapeutic effects in diseased tissue are disclosed. A first preferred embodiment of the apparatus relies on visual control; and a second preferred embodiment of the apparatus incorporates an integrated ultrasonic imaging and therapy transducer. The apparatus and method feature the close proximal placement of the ultrasound transducer to the diseased tissue to be treated, resulting in less attenuation of the beam and deposition of a greater fraction of the total emitted ultrasound energy in the selected portion of the diseased tissue. The ultrasound energy passes atraumatically through the urethral wall and other tissue not targeted. At the focal point of the ultrasound energy, substantial heating of diseased tissue to produce hyperthermal effects therein occurs, and even higher thermotherapeutic temperatures are attainable to produce coagulative necrosis of diseased tissue.

20 Claims, 4 Drawing Sheets

APPARATUS AND METHOD FOR TRANSURETHRAL FOCUSSED ULTRASOUND THERAPY

BACKGROUND OF THE INVENTION

This invention relates to an apparatus and method for the treatment of benign prostatic hyperplasia (BPH), prostate cancer, and other diseases by application of focussed ultrasonic energy from a probe placed near the site of the lesion.

BPH is a very common disease in men over 50 years of age, in which swelling of the prostate results in obstruction of the urethra and consequent inability or difficulty in urinating. In its early stages it causes discomfort and inconvenience. Permitted to progress, it can result in severe pain and serious consequences. It is traditionally treated by transurethral resection of the prostate (TURP), a surgical procedure with good effectiveness but an unfortunate level of pain, blood loss, morbidity, complications, expense, lost time, and in some cases death. Other methods, using lasers or radio frequency or microwave energy, have not been proved to approach TURP in effectiveness. A method combining high effectiveness with fewer short-term bad effects than TURP is still urgently required.

Prostate cancer is the second leading cause of cancer-related death in men. In its early stages it can be treated successfully by radical prostatectomy, but this procedure has all of the disadvantages of TURP and in addition often results in incontinence, impotence, or both. Prostate cancer can also be treated by radiation therapy, but similar serious side effects are common if a sufficient dose is used to have a good chance of a favorable result. A curative method with less initial trauma is needed. More advanced prostate cancer is also treated by radical prostatectomy or radiation therapy, but this procedure usually does not result in cure, though it may achieve palliation. Since less is accomplished in these cases, a less invasive method is even more necessary.

Ultrasound is well known to urologists for its ability to image a volume of tissue, creating pictorial slices without the need to cut. It can do this because ultrasonic waves are transmitted through tissue without being too strongly attenuated, yet, because there is significant absorption by tissue, intense ultrasound can produce very substantial heating in the interior of an organ. The goal in exploiting this effect is to create a large ultrasound intensity at the interior region to be treated while minimizing the ultrasound intensity in tissue that is to be spared. Prior attempts have been made to use the capabilities of focussed ultrasound for treatment of BPH and prostate cancer. One approach utilizes extracorporeal ultrasound focussed from outside the body; another uses a transrectal probe.

U.S. Pat. No. 5,344,435, to Turner et al. describes the transurethral application of unfocussed ultrasound energy for the treatment of prostatic disease. The disclosed apparatus, however, does not exploit the ability of ultrasound to reach a focus within the tissue, and thus to deliver a higher intensity at an internal point than is present at the urethral wall. Accordingly, and despite the use of urethral cooling, the inventors do not recommend temperatures greater than 48° C. Use of these temperatures diffusely in the prostate may be of some clinical value, but does not produce effects comparable to application of higher temperatures in a sharply defined volume of tissue, as taught in the present invention.

The apparatus of Turner et al. '435 operates in what is generally termed a hyperthermal mode. Energy transfer utilizing the apparatus of Turner et al. '435 is by radiation, that is, energy is transmitted from a source within the apparatus into a treatment volume much larger than the source itself. As a consequence of the hyperthermal irradiation temperature being limited to a maximum of 48° C., the diseased prostatic tissue must be irradiated for relatively long periods of time, often up to 60 minutes or more. This is disadvantageous in that it requires the patient to be immobilized during such lengthy treatment sessions.

When a transrectal probe is used, the ultrasound must pass through 4 cm or more of healthy tissue before reaching the tissue that is to be destroyed. If the probe is outside the body, the ultrasound must pass through an even greater depth of healthy tissue. In either case, the large distance between the probe and the tissue to be treated is disadvantageous because it increases the difficulty of targeting the ultrasound accurately, because healthy tissue is exposed to the potentially damaging effects of high intensity ultrasound, and because a higher initial power must be used to make up for attenuation in tissue between the probe and the target.

A further drawback to prior systems is that they focus the ultrasound at peak intensity on each individual volume of tissue to be treated. This requires extremely accurate targeting, generally requiring an elaborate and costly targeting system such as diagnostic ultrasound. It further requires the provision of accurate relative motion between the probe and the patient. Because of the high power required to compensate for or attenuation, and because of the accurate targeting required, prior art systems are extremely expensive, costing well over one hundred thousand dollars and in some cases many times more.

SUMMARY OF THE INVENTION

The broad principal objects of the present invention are to provide a device capable of treating BPH, prostate cancer, and other diseases by the application of high intensity ultrasound; to permit the treatment to be minimally traumatic by avoiding incision of any tissue and by entering only a single body cavity; to minimize damage to any tissue other than that which is to be treated; to minimize the required power output from the device so as to avoid unnecessary heating of nearby tissue; to simplify the monitoring procedure by using direct endoscopic visualization as far as possible; to minimize the cost of the treatment; to permit treatment without the requirement for anesthesia beyond topical agents such as lidocaine, so that the procedure is no more painful or acutely traumatic than examination with a flexible cystoscope; to permit treatment in which the urethra is neither pierced nor heated, and treatment of the prostatic parenchyma is well controlled; and to permit treatment in which post procedure catheterization is unnecessary, and such that patients without comorbidities can be treated at a medical services-providing facility such as a hospital, clinic, or even at a doctor's office, on an out-patient basis.

A further specific object of the present invention is the provision of a compact, intraluminal device which produces a focussed beam of ultrasound energy, and utilizes a single ultrasound transducer consisting of one or more piezoelectric elements. The device is capable of causing greater than hyperthermal therapeutic temperatures in selected regions of diseased tissue of a body organ in a particular area of the body, without causing the temperature in surrounding non-diseased tissue or in adjacent anatomical areas to be raised to damaging levels, thereby enabling the device to be much simplified by being able to dispense with the need for means for cooling adjacent non-diseased tissue and organs not being treated, to avoid thermal damage thereto. The device is also capable of effecting a course of therapy in a shorter period of time than is required for a course of therapy utilizing unfocussed radiating ultrasound energy in a hyperthermal mode of operation having a much lower maximum temperature limitation, as is necessary to avoid damage to surrounding non-diseased tissue and other anatomical areas.

A still further specific object of the present invention is the provision of a transurethral focussed ultrasound device for the treatment of BPH and other diseases of the prostate, having the above features, and which, because of the faster course of therapy, is simpler in design than a device for hyperthermal treatment, and which is able to dispense with the need for a urine drainage system because of the much shorter period of time the device is required to be present in the prostatic urethra of the patient during administration of a course of therapy. The present apparatus, in fact, when operationally positioned, does not need to extend beyond the prostatic urethra, either to the bladder neck or further into the bladder itself.

The novel apparatus and method of this invention are based on a therapeutic modality which we have termed Transurethral Ultrasound Therapy (TUT). This treatment modality utilizes the application of focussed ultrasound energy to the prostate from a probe in the prostatic urethra to effect hyperthermal or above hyperthermal heating of selected diseased prostatic tissue to be treated, thereby causing coagulative necrosis of the diseased tissue. The great advantage of the apparatus according to the present invention utilizing TUT is the superiority of the geometrical aspects of the treatment; the ultrasonic energy wave only has to travel about 1 cm through tissue. This is about one quarter as far as for transrectal application and represents a still greater advantage over extracorporeal application. The improved geometrical factors resulting from use of the apparatus of the present invention utilizing the TUT therapeutic modality allows the ultrasound energy to be focussed into a defined tissue volume, with minimal intensity being directed at tissue further away from the source. There is far less attenuation in this short path length, so the probe need not emit a great excess of ultrasound energy to compensate for attenuation. At the same time, non-diseased tissue nearer to the energy source is spared, because the ultrasound energy intensity in those areas is low. Because the TUT probe resides in the urethra, direct cystoscopic observation is a great aid in locating the probe, eliminating the need for more expensive monitoring systems. Further, while some transurethral devices can be uncomfortable, the improved geometry of the apparatus of the present invention allows a small, non-traumatic probe to be used. The TUT apparatus therefore combines high effectiveness with low invasiveness similar to flexible cystoscopy, which is commonly performed with only topical lidocaine jelly.

Certain further advantages arise out of operation of the present apparatus utilizing a high intensity, focussed beam of ultrasound energy. One advantage is that higher therapeutic temperatures can be attained in more precisely defined diseased regions in the interior of the prostate than can be attained with conventional hyperthermal treatment. Because these regions are removed from anatomical regions where higher temperatures can cause damage, there is no need for the device to provide for cooling these other anatomical regions. The present apparatus, therefore, also offers the advantage of enabling the achievement of high temperature where it is called for, while enabling the maintenance of safe, lower temperatures in surrounding areas.

Another advantage of the present apparatus is that because of the higher therapeutic temperatures attainable with focussed ultrasound in the limited area of the diseased tissue, the duration of treatment is shortened considerably over the time required for the typical course of conventional hyperthermal treatment. A further benefit of the shortened treatment time utilizing the present apparatus is that a urine drainage system extending into the bladder is not required as part of the present apparatus. In devices utilizing conventional hyperthermal treatment, such a urine drainage system is necessary to remove the accumulation of urine forming in the patient's bladder over a lengthy treatment session.

The present apparatus, therefore, has the still further advantages of being considerably simpler in construction and being easier to manufacture by not requiring means for cooling adjacent tissue or means for urine drainage, although in certain embodiments of the apparatus, one or both of these features may optionally be present.

The utilization of a focussed beam of ultrasound energy in the present apparatus, moreover, enables the apparatus to be constructed utilizing a single ultrasonic transducer consisting of one or more piezoelectric elements. This is in contrast to devices of the radiating ultrasonic applicator type which require a plurality of transducers to produce an ultrasound energy field capable of being simultaneously radiated in many directions, usually omnidirectionally, into a volume considerably greater than the volume at the source.

All of the foregoing features and advantages of the present apparatus are lacking in the various apparatuses of the known prior art. Accordingly, the apparatus of the present invention is deemed to satisfy a need in the art for such a device and to make a novel and innovative contribution to the art in this field.

DETAILED DESCRIPTION OF PREFERRED EMBODIMENTS OF THE INVENTION

The heating effect of ultrasound depends on the intensity, or power per unit area, of the ultrasound. When the ultrasound is focussed into a spot whose area is small, the intensity is correspondingly high. If the same total power is spread over a larger area, the intensity is correspondingly lower. The amount of heat generated at a point in tissue, and thus the temperature increase that results, is generally proportional to the ultrasound intensity at that point.

The TUT apparatus of the present invention uses a probe in the urethra quite close to the tissue to be treated. One important advantage of being able to treat the diseased tissue from such close proximity is that a high relative aperture can be utilized. The relative aperture, n, is defined as the focal length divided by the diameter of the aperture through which ultrasound energy is emitted. If a small value of n is used, the ultrasound energy intensity at the focus is much higher than the intensity either nearer to the aperture or beyond the focus. Accordingly, tissue a distance from the focus is spared.

Figure 1:
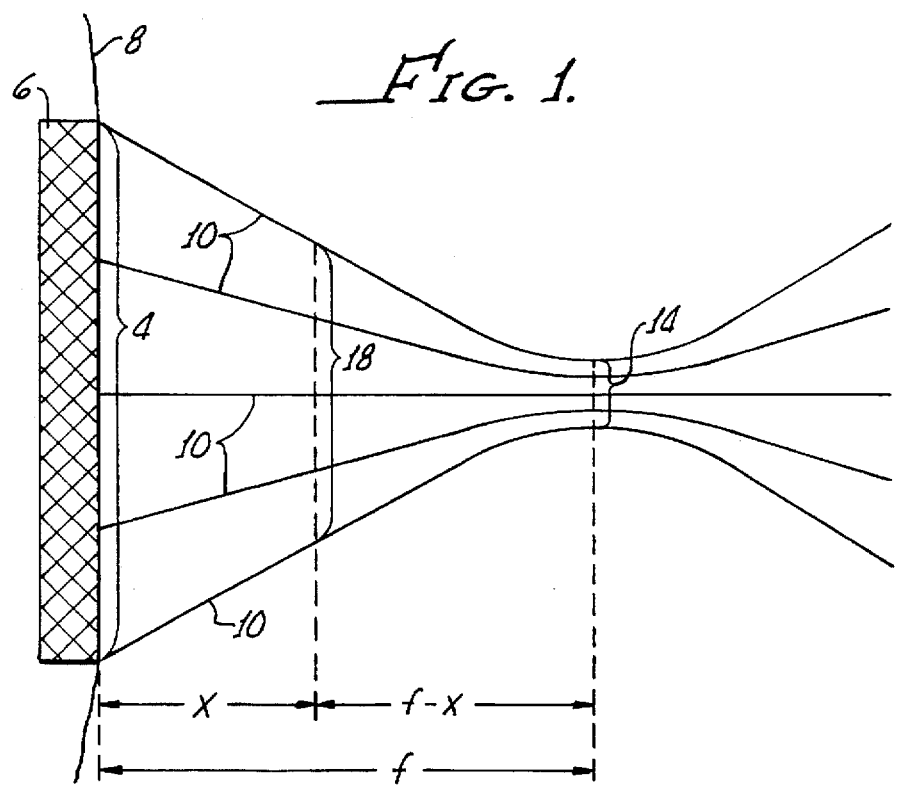
FIG. 1 shows an ultrasound emission pattern from a circular aperture of an ultrasound probe according to the present invention.

This is expressed quantitatively by the following formulae, wherein the emission of ultrasound from circular aperture 4 of ultrasound probe 6 in FIG. 1 is considered. Aperture 4 has a diameter A and area $(\pi/4)A^2$, and is in contact with tissue surface 8. The emitting probe is of a focussing configuration causing ultrasound energy beam 10 to be focussed at focal plane 14 a distance f into the tissue. If the power emitted from the aperture is W watts, the initial intensity $I_o$, or power per unit area, is given by $$I_o = W/(\pi/4)A^2$$

At plane 18 a distance x from the aperture, or f-x from the focal plane, the volume of tissue exposed to the ultrasound has a circular cross section of area $[(\pi/4)A^2] \cdot [(f-x)/f]^2$. The intensity at x is therefore given by $$I_x = W/[(\pi/4)[A \cdot (f-x)/f]^2]$$

in the absence of attenuation. The ultrasound energy is, however, actually attenuated as it passes through tissue, so that $$I_{xa} = W \cdot \exp[-\mu x]/[(\pi/4)[A(f-x)/f]^2]$$

where μ is the attenuation per unit length, and has the approximate numerical value 0.16 v cm$^{-1}$, if v is the frequency expressed in megahertz (MHz).

The area of the exposed tissue at focal plane 14 does not drop to zero, as suggested by these equations. FIG. 1 shows that the focus is not infinitely sharp. At the focus, the diameter of the exposed tissue is given by diffraction theory as 1.2 nλ, where n is the relative aperture defined above, and λ is the wavelength of the ultrasound; in tissue its approximate numerical value in mm is 1.5/v, if v is expressed in MHz. The focal intensity $I_f$ is given by $$I_f = W \cdot \exp(-\mu f)/[(\pi/4)[1.2 \, n\lambda]^2]$$

These equations show that the ratio of intensity at the focus to initially emitted intensity is given by $$I_f/I_o = \exp(-\mu f)/[1.2 \, n\lambda]^2$$

Similarly, the ratio of the intensity at a distance (f-x) from the focus to the intensity at the focus is $$I_x/I_f = \exp[-\mu(x-f)] \cdot [1.2 \, n\lambda f/A(f-x)]^2$$

Thus, in order to minimize intensity in healthy tissue while delivering as much power as possible near the focus in the tissue to be treated, it is best to use a small relative aperture and a short focal length. The focal point should be in the tissue to be treated, so the focal length is about equal to the distance from the probe to the tissue to be treated. In other words, the probe should be as near as possible to the target. This configuration reduces the attenuation and therefore eliminates the need for very high power from the probe. The small relative aperture causes the intensity to be substantially less at a distance from the focal point. Locating the probe in the urethra, about four times nearer to the tissue to be treated than with a transrectal procedure, is the only way to meet these two requirements in the case of prostate therapy. The first preferred embodiment described below has a focal length of 12 mm and an aperture of 8 mm, for a relative aperture of 1.5. When operated at a frequency of 5 MHz and emitted ultrasound power of 10 watts, it delivers over 1600 watts/cm$^2$ to the focal point. In order to deliver this much power to the focus, a transducer operating at 5 MHz, 40 mm from the focal point, would have to emit over 60 watts of ultrasound power. At this power level, it could not be operated continuously for a long enough time to produce extensive coagulation without a cooling system that would be impractical for use within the body. For best results, the relative aperture should be no more than 1.7 and the focal length not more than 20 mm. A relative aperture, n, of 1.7 is often denoted as f/1.7 optics.

A further advantage of the invention is that it makes possible the use of a higher ultrasound frequency. The length of the lesion, in the direction parallel to the direction of propagation of the ultrasound, is proportional to the depth of focus. But the depth of focus, in turn, is inversely proportional to the ultrasound frequency. Use of a low frequency, therefore, tends to produce an elongated lesion, which is disadvantageous because tissue in critical regions may be heated, with the danger of harm to the patient. Anatomical regions placed at risk by a large depth of field, and thus by a low ultrasound frequency, include the prostatic capsule, anterior rectal wall, external sphincter, and neurovascular bundle. For this reason it is desirable to use as high a frequency as possible. But since ultrasound attenuation increases with frequency, the range of the treatment is limited more severely at higher frequency. The apparatus of the current invention permits use of higher frequency because the ultrasound does not need to travel as far through tissue as is required with transrectal or extracorporeal ultrasound. Because a higher frequency can be used, prostate disease is treated with less risk of harm to critical structures of the patient's anatomy. For the typical 1 cm distance utilized by the apparatus of the current invention, 20% of the ultrasound energy would be transmitted to the focal point even at a frequency as high as 10 MHz, while 87% would be transmitted at a frequency of 1 MHz. The typical 4 cm distance required for transrectal treatment requires a frequency no higher than 2.5 MHz to be used in order for 20% of the emitted ultrasound energy to reach the focal point. While lower transmission can be tolerated, it requires a more expensive high power transducer, and results in deposition of substantial quantities of heat in non-diseased tissue that is not intended to be affected. Prior systems therefore compromise by using a lower ultrasound frequency than would be desired for maximum patient safety.

Two preferred embodiments of an apparatus and method for transurethral ultrasound therapy, according to the present invention, will now be described. The first embodiment is used under visual control. Its advantages include efficacy, low cost, and lack of trauma. Its most preferred use is for treatment of BPH, although it is also useful for treatment of prostate cancer. The second embodiment combines therapeutic and imaging ultrasound. It allows the position of the focal spot within the tissue to be controlled to within less than 1 mm, and permits the evolving effect to be monitored in real time. In addition to BPH, this embodiment is particularly useful in the treatment of prostate cancer.

First Preferred Embodiment

The first preferred embodiment of an apparatus according to the present invention is a therapeutic ultrasound system powered by a simple, inexpensive generator. This system relies on visual control and is used without simultaneous ultrasonic imaging. A reusable flexible imaging/illumination bundle is included within the catheter.

Figure 2:
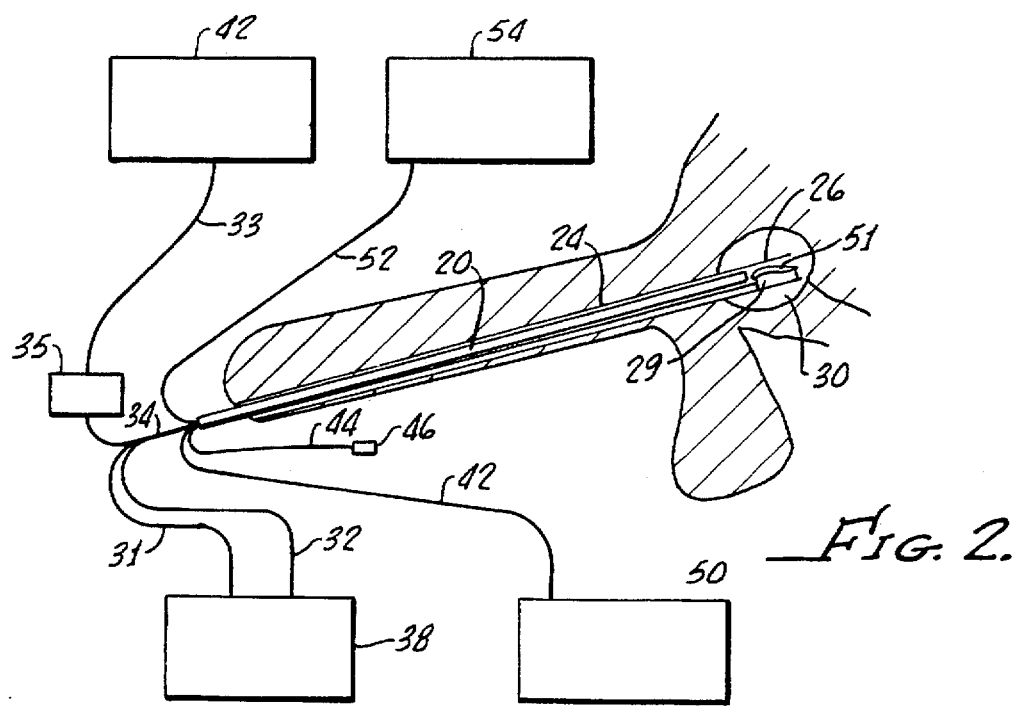
FIG. 2 shows a first preferred embodiment of the apparatus according to the present invention in anatomical perspective.

Referring to FIG. 2, catheter 20 is inserted via the patient's urethra 24 until it reaches prostatic urethra 26 within prostate 30. Ultrasound probe 29 extends beyond catheter 20. Probe lines 31, 32, and 33 are combined into bundle 34 which passes through the interior of catheter 20. Probe lines 31 and 32 carry cooling water between supply 38 and ultrasound probe 29. Probe line 33 carries radio frequency electricity between power unit 42 and ultrasound probe 29. Matching network 35 minimizes inefficiencies in coupling of the radio frequency electrical power into the transducer. Flexible endoscope 44, which terminates in eyepiece 46, also passes through the interior of catheter 20 to provide a view of prostatic urethra 26 and probe 29. Cable 48 carries illumination from light source 50 to endoscope 44. Positioning balloon 51 extends beyond catheter 20 and is inflated with fluid from reservoir 54 carried through tube 52.

Figure 3:
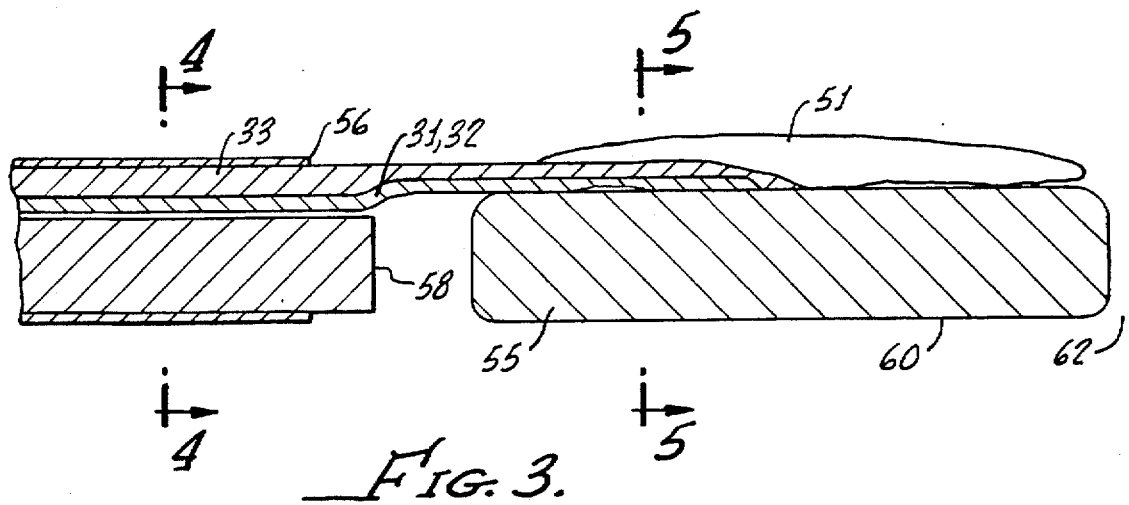
FIG. 3 shows an ultrasound transducer housing according to the present invention.

FIG. 3 shows transducer housing 55 of ultrasound probe 29 extending from proximal end 56 of catheter 20. Lines 31–33 are attached to the transducer housing. Distal end 58 of flexible endoscope 44 extends slightly out of the catheter. Positioning balloon 51 is adjacent to the transducer housing. When balloon 51 is inflated, front face 60 of transducer housing 55 is pressed firmly against wall 62 of prostatic urethra 26 assuring good acoustic coupling of ultrasound energy into prostatic tissue.

Figure 4:
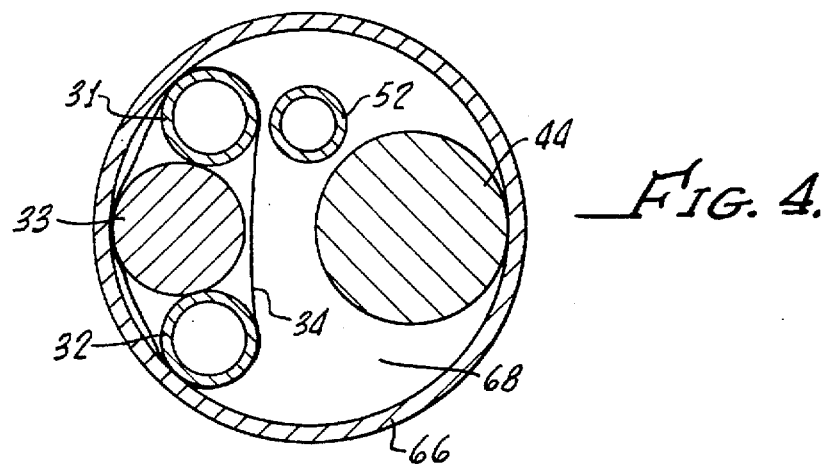
FIG. 4 shows a cross-sectional view through A—A of the housing of FIG. 3.
Figure 5:
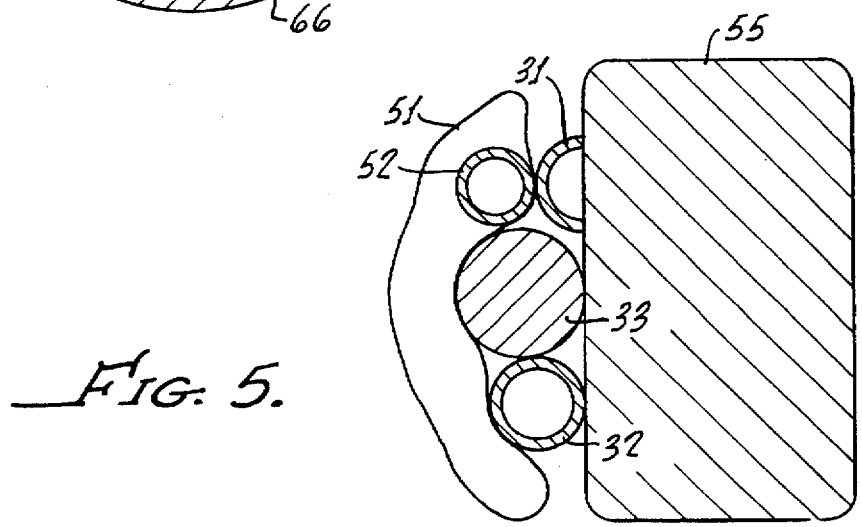
FIG. 5 shows a cross-sectional view through B—B of the housing of FIG. 3.

FIG. 4 shows section A—A of FIG. 3. Wall 66 of catheter 20 defines lumen 68, which accommodates bundle 34, endoscope 44, and tube 52, which is used to inflate positioning balloon 51. FIG. 5 shows section B—B of FIG. 3. Probe line 32 carries a cooling liquid from supply 38, which preferably includes a chiller to lower the temperature of the cooling liquid below room temperature, to transducer housing 55. Probe line 31 carries return liquid from the transducer housing to supply 38, allowing continuous flow of cooling liquid. Probe line 33 provides power to the transducer and may carry other electrical signals.

Figure 6A:
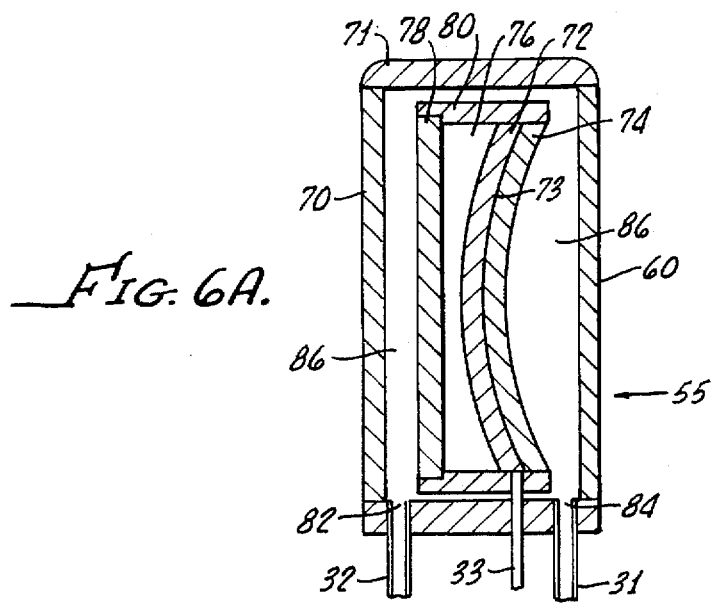
FIG. 6A shows a detailed view of one embodiment of the ultrasound probe of the apparatus of FIG. 2, including the transducer, focussing means and coupling means.
Figure 7:
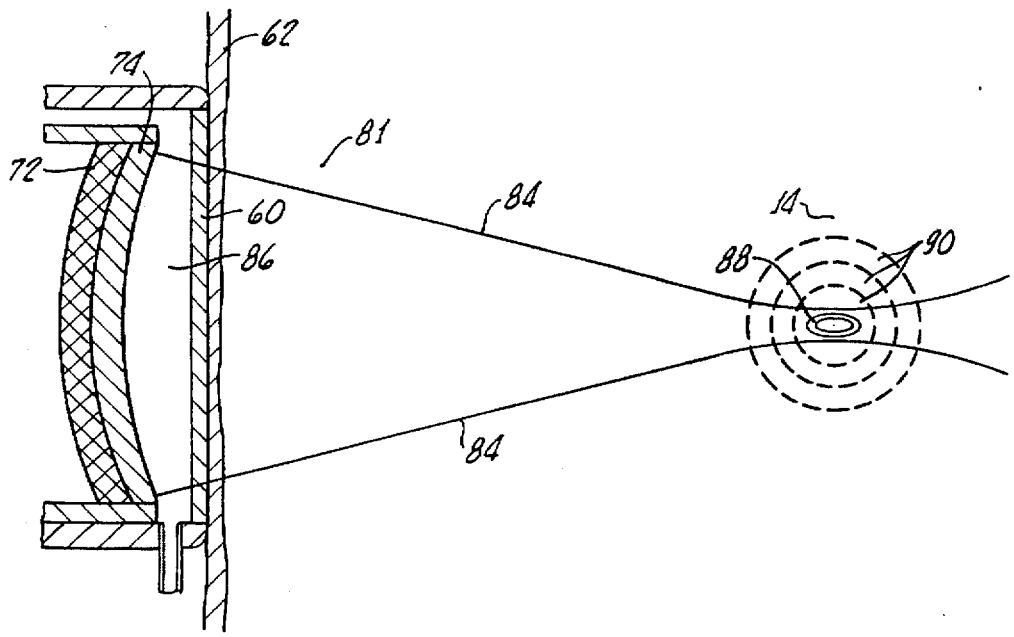
FIG. 7 shows a focussed ultrasound beam emanating from the ultrasound probe of FIG. 6.

FIG. 6A shows ultrasound probe 29 in further detail. Transducer 72, which includes a single ultrasonic transducer consisting of one or more piezoelectric elements made of a piezoelectric material, such as hard lead zirconate/lead titanate piezoelectric ceramic, receives radio frequency power from line 33, and vibrates in response to create ultrasound energy. Because of the concavity of front surface 73 of transducer 72, the ultrasound energy is focussed as shown in FIG. 7. The ultrasound energy is coupled by quarter wave plate 74, minimizing reflection back to the transducer, and passes through front face 60 of transducer housing 55. The transducer and quarter wave plate are supported by back plate 78 and periphery 80, defining gap 76, which damps backward propagation of ultrasound. The outer housing comprises front face 60, back face 70, and periphery 71 of transducer housing 55. If necessary, cooling liquid from line 32 enters the housing at inlet 82, moves through passage 86, and exits through outlet 84 to line 31, carrying off heat generated within the transducer housing. This heat could otherwise damage the transducer and quarter wave plate, and could cause undesirable heating of the urethral wall.

Figure 6B:
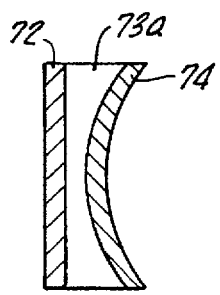
FIGS. 6B–6D show alternative embodiments of the transducer, focussing means and/or coupling means of the ultrasound probe means of the apparatus of the present invention.
Figure 6C:
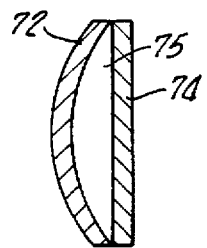
Figure 6D:
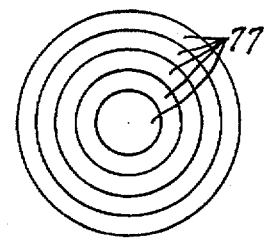

FIGS. 6B–6D show alternative techniques for achieving focussing of the ultrasonic energy. In FIG. 6B the transducer 72 is flat rather than concave as in FIG. 6A, and planoconcave lens 73a, of a suitable material that transmits ultrasound, provides the focussing. In FIG. 6C transducer 72 is concave but quarter wave plate 74 is flat, with gap 75 filled by a material that transmits ultrasound. In FIG. 6D the transducer comprises a plurality of flat, ring-shaped elements 77. Electrical energy is provided to each ring with a phase that is advanced with the respect to the phase of electrical energy supplied to the next inner ring, creating a phased array that focusses ultrasound energy.

In use, catheter 20 and probe 29 are advanced to the prostatic urethra. Endoscope 44 is used to position the probe as desired. When the position is correct, positioning balloon 51 is inflated to fix the probe's position and to assure good contact between front face 60 and the urethral wall. Blood and other bodily fluids are thus excluded from the area between the transducer and the prostatic tissue. When the position has been fixed, power from power supply 42 is applied to transducer 72 via line 33 and matching network 35.

As illustrated in FIG. 7, ultrasound energy from transducer 72 passes through quarter wave plate 74, cooling liquid in passage 86, front wall 60 of the transducer housing, and urethral wall 62, then entering the prostatic parenchyma 81. Ultrasound energy is absorbed in the prostatic parenchyma, depositing energy as heat generally proportional to the ultrasound intensity. Because of the focussing effect, outer rays 84 converge so that the intensity is greatest near focal plane 14. As a result, substantial heat is deposited in central region 88 while much less heat is deposited elsewhere within the prostate. In regions beyond the focal plane, attenuation and spreading of the ultrasound over a larger area combine to cause more rapid decrease in intensity. This has the desirable effect of tending to spare tissue beyond the focal point, including several critical structures. When the temperature of central region 88 has increased, a generally spherical surrounding volume is heated by thermal conduction. Isotherms 90 define spherical shells with temperature increasing toward the center. The ultrasound power, frequency, and duration can be chosen so that an ultrasound exposure of between 30 seconds and 10 minutes causes a volume of several cubic centimeters to be heated to a temperature of at least 60° C. It is known in the art that prostate tissue heated to this temperature undergoes coagulative necrosis and is subsequently resorbed. The apparatus of the present invention, therefore, causes elimination of a clinically useful volume of tissue without frequent retargeting of the ultrasound, and without the need for a complex system to produce and monitor motion of the probe relative to the tissue.

According to a particularly preferred method, the concentration of generated heat in tissue within central region 88 is increased still further. It is well known that the ultrasonic propagation properties of tissue are modified by changes in the tissue such as coagulative necrosis. N. L. Bush, I. Rivens, G. R. ter Haar, and J. C. Bamber have reported measurements of this effect in an article titled "Acoustic properties of lesions generated with an ultrasound therapy system" appearing in *Ultrasound in Medicine and Biology* Volume 19, Number 9, pages 789–801. They find that attenuation of acoustic waves is increased when tissue has been sufficiently heated to undergo coagulative necrosis. The average increase in their measured values was over 98%. In the particularly preferred method, ultrasound is applied at a relatively high intensity for a short time, so that tissue is denatured in central region 88. Other regions of the tissue, where the ultrasound intensity is lower, are not heated as much and are not denatured. The ultrasound power is then decreased, preferably in a short time of about 5 seconds or less to prevent unnecessary heat loss, to a level at which tissue away from the focus is not significantly heated. In central region 88, because of the increased attenuation in the tissue that has been denatured, heat continues to be deposited at a high rate. This additional heat then moves by thermal conduction to tissue in the region surrounding the focus. A large, targeted volume of tissue is thus treated without excessive heating of tissue that is not targeted. The ultrasound power can be decreased by the operator after a predetermined time interval or according to some other criterion. This power change is preferably accomplished by an automatic system responsive to a timer or to sensing of some condition by means familiar to those skilled in the art. In one embodiment, the reflected ultrasound echo is detected by the ultrasound transducer. This is accomplished by means similar to the second preferred embodiment described below, but a simpler system can be used because there is no need to form an ultrasound image. Thus the reflection of some or all of the ultrasound used to heat the tissue can be measured. The changes induced in tissue near the focal point cause changes in the reflected ultrasound including changes in reflectivity, sound velocity, and others. In one embodiment, the change in reflected ultrasound intensity is detected. This change signals that tissue near the focal point has been denatured. The ultrasound power is then decreased, either automatically or by operator intervention. It is also possible for the device to respond automatically to detection of a fault condition. For example, the temperature of the cooling fluid exiting the transducer housing can be measured by means such as a thermocouple placed in outlet line 31. If this temperature is excessive, indicating that the electrical energy supplied to the transducer is not being efficiently converted to ultrasound energy coupled into the interior of the prostate, automatic circuitry responsive to this temperature can lower the electrical power level, avoiding damage to the transducer. Alternatively, as is known in the art, a conventional ultrasonic imaging probe could be placed in the rectum to monitor the placement of the transurethral device and/or the development of the lesion.

Because the probe is very small and is delivered by a flexible system, and because the urethral wall is neither pierced nor excessively heated, discomfort during the procedure is no worse than in flexible cystoscopy, which is routinely performed without anesthesia other than topical lidocaine. The need for postprocedure catheterization is limited by the absence of trauma to the urethral wall, so that a patient without complications or comorbidities can return home the same day he is treated.

Second Preferred Embodiment

Figure 8:
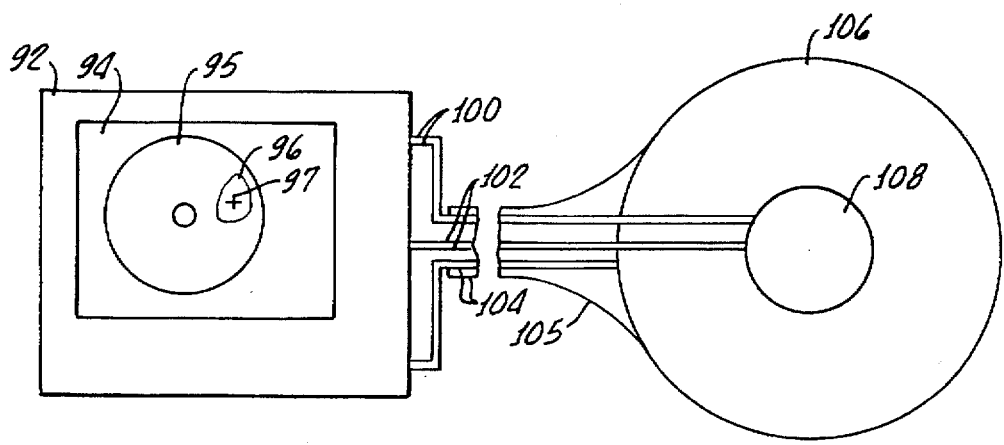
FIG. 8 shows a second preferred embodiment of the apparatus according to the present invention with a transurethral imaging ultrasound probe.

A second preferred embodiment of an apparatus according to the present invention integrates the therapeutic ultrasound transducer with a transurethral imaging ultrasound probe, as shown in FIG. 8. This system is generally known to those skilled in the art, but in the apparatus of this preferred embodiment of the present invention, is sized for use in a small conduit such as the urethra. Its dimensions, construction, and method for delivery and endoscopic visualization are similar to those of the apparatus of FIGS. 2–6. Power and control unit 92 provides electrical energy to excite transducer 106 for both imaging and therapeutic purposes. All of these lines are contained in cable 105. Ultrasonic image 95 is generated by mechanical motion or by an electric array, both of which techniques are known in the art, and is displayed on screen 94. For therapeutic use where a small numerical aperture is preferred, power is provided to all of transducer 106.

For imaging, which requires greater depth of field, power is provided only to central portion 108 of transducer 106.

The combination system provides transurethral ultrasonograms in real time before, during and after therapy. Therapy may be interrupted briefly to acquire an updated sonogram, allowing the progress of the treatment to be monitored. Location of and positioning of the apparatus in the parenchyma lesion within the prostate is precise, because heating tissue to a temperature above 60° C. results in a bright area 96 on the ultrasonogram. Internally generated symbol 97 in the ultrasound image specifies the focal point of the ultrasound therapy transducer to an accuracy better than one millimeter. Because of its proximity to the lesion, the transurethral imaging transducer shows the development of echogenic zone 96 with great clarity. When probe 106 is so positioned that symbol 97 coincides with the image of tissue to be treated, the therapeutic ultrasound is known to be accurately targeted on that tissue. Round-trip attenuation of the diagnostic ultrasound and return echo is less than 85 percent, for a frequency of 5 MHz and 12 mm distance from probe to focus. This allows an excellent signal-to-noise ratio. Images of treated zones can be stored in memory and displayed even after the immediate echogenicity has faded. Multiple lesions, precisely targeted and monitored for size, can be produced in minimal time. It is also possible to monitor therapeutic ultrasound therapy using a conventional transrectal ultrasound probe.

Beyond its use for difficult BPH lesions, this system may offer the first effective minimally invasive system for treating prostate cancer. Focal lesions can be targeted for obliteration. In addition, as much as necessary of the prostatic parenchyma can be heated to coagulation temperatures. In the event of recurrent or residual tumor, a repeat procedure causes minimal morbidity. This system should approach or exceed the effectiveness of radical prostatectomy while preserving continence and sexual function in most cases, because of its low trauma.

In an alternative related use, hyperthermia from heating of the prostate with either embodiment of the device of this invention can be used in combination with ionizing radiation therapy. The combination of hyperthermia and ionizing radiation is known to be effective in treatment of malignant tumors. The tissue temperatures used in this application are lower than those required for coagulative necrosis, and preferably are less than 50° C.

While the invention has been described with particular reference to prostate diseases such as BPH and prostate cancer, there are many other organs, including but not limited to the heart, liver, urinary bladder, gall bladder, and organs of the circulatory system, that can be treated by devices within the scope of the invention.

The foregoing two preferred embodiments of the apparatus of the present invention are illustrative. Other embodiments of the apparatus, within the scope of the invention, which is established by the claims following hereinafter, will be recognized by those skilled in the art.

We claim:

1. An apparatus for treatment of diseases of the prostate in a mammalian body, said apparatus comprising:

(a) a generator of a radio frequency electrical signal, having a frequency in the range of from about 1 MHz to about 10 MHz, capable of generating a constant power level and capable of operating at said constant power level for a period of time of at least 30 seconds;

(b) a transurethral probe transducer housing containing a transducer and a substantially circular output aperture having an area that is substantially circular, and corresponding coupling means and focusing means therefor, for converting at least a portion of said electrical signal into a beam of ultrasound energy, said beam having an area and sufficient power to produce thermal effects in prostatic tissue and to cause coagulative necrosis in selected portions of diseased prostatic tissue, and for coupling said ultrasound energy into diseased prostatic tissue, and focusing said ultrasound energy at a focal plane, such that said area of said beam of ultrasound energy at said focal plane is less than said area of said aperture and forms a substantially circular spot;

(c) delivery means for transurethrally introducing the transurethral probe transducer housing into the prostatic urethra of a mammalian body; and (d) positioning means for fixing the transurethral probe transducer housing in a desired position in said prostatic urethra;

(e) at least one visualization means for enabling the remote observation of at least one of the positioning of the transurethral probe transducer housing, and the treatment of said diseased prostatic tissue, said visualization means being selected from the group (i–ii) consisting of:
  (i) endoscopic means for viewing the position of the transurethral probe transducer housing within the urethra, and
  (ii) diagnostic ultrasound means for generating an ultrasound imaging signal for producing an ultrasound image of at least a portion of the prostatic tissue to be treated.

2. The apparatus according to claim 1 wherein said delivery means is a tubular shaft housing having a proximal end, a distal end, an inner diameter, an outer diameter, a length, and at least one lumen extending therethrough, with the transurethral probe transducer housing cooperating with said delivery means and being positioned at said distal end of said delivery means.

3. The apparatus according to claim 1 in which said delivery means includes a flexible catheter having a proximal end, a distal end, and a longitudinal axis from said proximal end to said distal end, the maximum dimension of said catheter in a direction transverse to said longitudinal axis being not greater than 10 mm, with the transurethral probe transducer housing cooperating with said catheter and being positioned at said distal end of said catheter.

4. The apparatus according to claim 1 wherein said coupling means and said focusing means constitute a pair of elements selected from the group (i–iv) consisting of:
  (i) a concave transducer for focusing, in communication with a concave quarter wave plate for coupling;
  (ii) a planar transducer with a planoconcave lens made of an ultrasound transmitting material for focusing, in communication with a concave quarter wave plate for coupling;
  (iii) a concave transducer in cooperation with a planar quarter wave plate, with a gap therebetween filled with an ultrasound transmitting material, such that said transducer and said ultrasound transmitting material in said gap provide focusing; and said quarter wave plate provides coupling; and
  (iv) a transducer made of a plurality of flat, ring-shaped elements forming a phased array for focusing, and a planar quarter wave plate for coupling.

5. The apparatus according to claim 4 wherein said focusing means and said coupling means is (i).

6. The apparatus according to claim 1 in which said ultrasound energy is focussed with a relative aperture less than about 1.7.

7. The apparatus according to claim 1 in which less than 80 percent of the emitted ultrasound energy is absorbed before reaching said diseased prostate tissue to be treated.

8. The apparatus according to claim 1 further including cooling means for limiting at least one temperature selected from the group consisting of:
  (i) the temperature reached by said transducer and coupling means, and
  (ii) the temperature reached by surrounding prostatic and non-prostatic tissue nearest said transducer and said coupling means.

9. The apparatus according to claim 8 in which said cooling means includes a source of cooling liquid external to said apparatus, means for allowing said cooling liquid to flow continuously from said source into said apparatus and into close proximity the transurethral probe transducer housing, and means for further allowing said cooling liquid to flow, after being warmed by absorption of heat from the transurethral probe transducer housing, out of said apparatus.

10. The apparatus according to claim 1 in which said positioning means includes an inflatable balloon for holding the transurethral probe transducer housing at a selected position in said prostatic urethra.

11. The apparatus according to claim 1 in which the ultrasound power output from the transurethral probe transducer housing required to produce coagulative necrosis does not exceed 10 watts.

12. The apparatus according to claim 1 wherein when said diagnostic ultrasound means is selected, total attenuation of said ultrasound imaging signal.

13. The apparatus according to claim 1 in which said generator of a radio frequency electrical signal includes means to vary the power during treatment according to a preprogrammed regime.

14. The apparatus according to claim 1 in which said generator of a radio frequency electrical signal includes means to detect a fault condition and automatically decrease the power conducted to said transducer in response to the detection of a fault condition.

15. The apparatus according to claim 1 further including intensity altering means for altering intensity of the ultrasound energy from a first predetermined level to a second, lower, predetermined level within a time not exceeding 5 seconds.

16. The apparatus according to claim 15 in which said intensity altering means includes means for altering said ultrasound intensity automatically at a preset time interval after irradiation with said ultrasound energy has begun.

17. The apparatus according to claim 1 further including means for detecting a return ultrasound echo from tissue in the vicinity of the focal point of the ultrasound energy.

18. The apparatus according to claim 17 in which at least one characteristic of said return ultrasound echo is used to define a point in time at which to alter the ultrasound energy intensity from a first predetermined level to a second predetermined level.

19. A method for treating of disease in a mammal, said method comprising: irradiating a selected portion of diseased tissue in a mammalian body with ultrasound energy having a frequency in the range of from 1–10 MHz, utilizing an apparatus comprising:

(a) a generator of a radio frequency electrical signal, having a frequency in the range of from about 1 MHz to about 10 MHz, capable of generating a constant power level and capable of operating at said constant power level for a period of time of at least 30 seconds;

(b) the transurethral probe transducer housing including a single transducer with one or more piezoelectric elements and a substantially circular output aperture having an area that is substantially circular, and corresponding coupling means and focusing means therefor, for converting at least a portion of said electrical signal into a beam of ultrasound energy, said beam having an area and sufficient power to produce thermal effects in prostatic tissue and to cause coagulative necrosis in selected portions of diseased prostate tissue, and for coupling said ultrasound energy into diseased prostatic tissue, and focusing said ultrasound energy at a focal plane such that said area of said beam of ultrasound energy at said focal plane is less than said area of said aperture and forms a substantially circular spot;

(c) delivery means for transurethrally introducing the transurethral probe transducer housing into the prostatic urethra of a mammalian body; and (d) positioning means for fixing the transurethral probe transducer housing in a desired position in said prostatic urethra;

(e) at least one visualization means for enabling the remote observation of at least one of the positioning of the transurethral probe transducer housing, and the treatment of said diseased prostatic tissue, said visualization means being selected from the group (i–ii) consisting of:

(i) endoscopic means for viewing the position of the transurethral probe transducer housing within the urethra, and (ii) diagnostic ultrasound means for generating an ultrasound imaging signal for producing an ultrasound image of at least a portion of the prostatic tissue to be treated;

such that:
said ultrasound energy is coupled into said diseased tissue to cause heat deposition near a focal point in the interior of said mammalian body;

the intensity of said ultrasound energy is initially high enough to cause denaturation and change in ultrasound attenuation properties in a small region of said diseased tissue near said focal point, within a time which is sufficiently short to prevent coagulative necrosis in non-diseased regions of tissue surrounding said diseased tissue; and said intensity of said ultrasound energy is then reduced so that heat deposition occurs preferentially in said small region of said diseased tissue where ultrasound attenuation properties have been changed.

20. A method of treatment of prostate cancer comprising: utilizing ultrasound energy to heat tumorous prostatic tissue and produce hyperthermal effects therein, said ultrasound energy being supplied by an apparatus comprising:

(a) a generator of a radio frequency electrical signal, having a frequency in the range of from about 1 MHz to about 10 MHz, capable of generating a constant power level and capable of operating at said constant power level for a period of time of at least 30 seconds;

(b) the transurethral probe transducer housing including a single transducer with one or more piezoelectric elements and an output aperture having an area, and corresponding focusing means and coupling means therefor, for converting at least a portion of said electrical signal into a beam of ultrasound energy, said beam having an area and sufficient power to produce thermal effects in prostatic tissue and to cause coagulative necrosis in selected portions of diseased prostatic tissue, and for coupling said ultrasound energy into diseased prostatic tissue, and focusing said ultrasound energy at a focal plane such that said area of said beam of ultrasound energy at said focal point is less than said area of said aperture;

(c) delivery means for transurethrally introducing the transurethral probe transducer housing into the prostatic urethra of a mammalian body; and (d) positioning means for fixing the transurethral probe transducer housing in a desired position in said prostatic urethra;

(e) at least one visualization means for enabling the remote observation of at least one of the positioning of the transurethral probe transducer housing, and the treatment of said at diseased prostatic tissue, said visualization means being selected from the group (i–ii) consisting of:

(i) endoscopic means for viewing the position of the transurethral probe transducer housing within the urethra, and (ii) diagnostic ultrasound means for generating an ultrasound imaging signal for producing an ultrasound image of at least a portion of the prostatic tissue to be treated;

and applying ionizing radiation therapy to said tumorous prostatic tissue in a mode selected from the group (iii–iv) consisting of:

(iii) prior to application of said ultrasound energy; and (iv) simultaneous with application of said ultrasound energy.

* * * * *